(12) United States Patent
Härle

(10) Patent No.: US 6,183,768 B1
(45) Date of Patent: Feb. 6, 2001

(54) IMPLANTABLE MEDICINE RELEASING CORPUSCLES AND METHOD OF MAKING, IMPLANTING AND REMOVING THE SAME

(76) Inventor: Anton Härle, Drechslerweg 40, D-48161 Münster (DE)

( * ) Notice: Under 35 U.S.C. 154(b), the term of this patent shall be extended for 0 days.

(21) Appl. No.: 09/281,179

(22) Filed: Feb. 18, 1999

Related U.S. Application Data

(63) Continuation-in-part of application No. 08/686,898, filed on Jul. 25, 1996, now abandoned.

(30) Foreign Application Priority Data

Jul. 26, 1995 (DE) .............................. 195 27 306

(51) Int. Cl.[7] ...................................... A61F 2/02
(52) U.S. Cl. .............................................. 424/423
(58) Field of Search ............................................ 424/423

(56) References Cited

U.S. PATENT DOCUMENTS 4,839,215 * 6/1989 Starling ................................ 428/131

* cited by examiner

Primary Examiner—Carlos A. Azpuru
(74) Attorney, Agent, or Firm—Peter K. Kontler

(57) ABSTRACT

Corpuscles for implantation into or at body tissue have carriers of biologically inert material, and such carriers contain medicine which is distributed therein for release into body tissue upon completion of the implanting operation. The configuration of the carriers departs from a spherical or an exact spheroidal shape. The end sections of the carriers can have conical, frustoconical, semiellipsoidal, or semispherical shapes and can consist of pairs of identical or different segments. The central sections of the carriers can resemble barrels, or their central longitudinal cross sections can have conical, elliptical, straight or other outlines. The carriers have central or substantially central longitudinal passages for a filament which supports a surgically implantable composition constituting a row or file or string of two or more identical and/or different carriers. The transverse cross sections of the carriers can have circular, elliptical, polygonal and/or other outlines. An advantage of the corpuscles is that the surface-to-volume ratio of their carriers is more satisfactory than that of the carriers forming part of conventional corpuscles so that they can be readily withdrawn from the body.

51 Claims, 1 Drawing Sheet

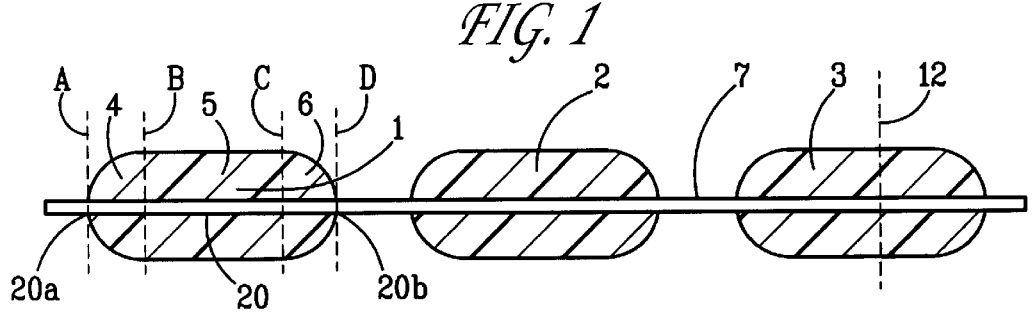
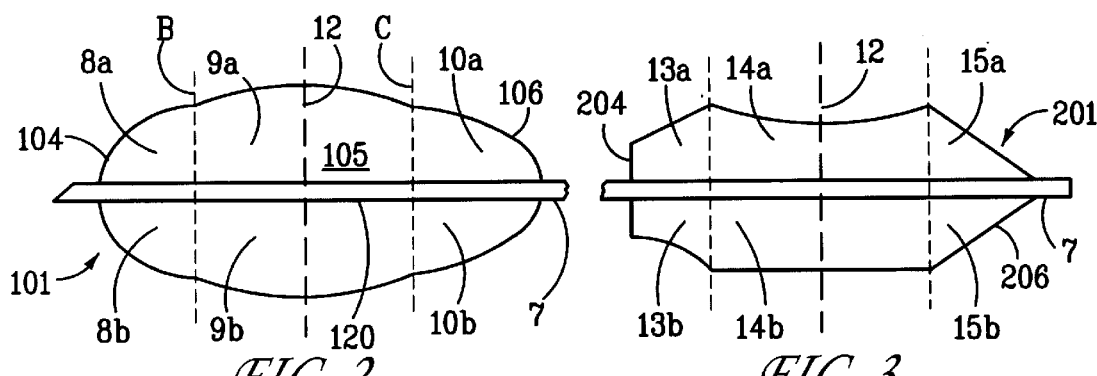
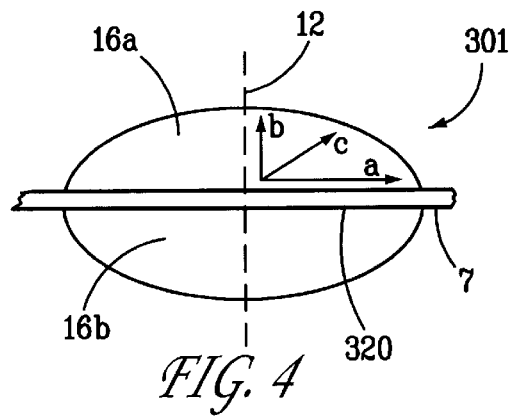
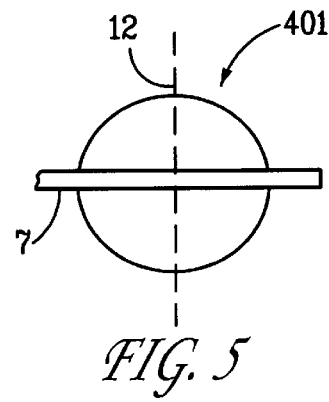
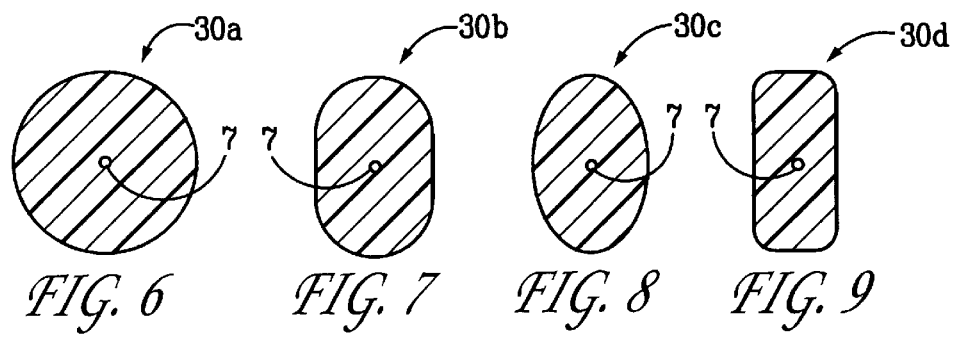

IMPLANTABLE MEDICINE RELEASING CORPUSCLES AND METHOD OF MAKING, IMPLANTING AND REMOVING THE SAME

CROSS-REFERENCE TO RELATED CASE

This is a continuation-in-part of my U.S. patent application Ser. No. 08/686,898 filed Jul. 25, 1996, now abandoned.

BACKGROUND OF THE INVENTION

The invention relates to improvements in particles (hereinafter called corpuscles) which contain a biologically inert material and medicine distributed in the inert material. Corpuscles of such character are utilized for implantation into animal bodies so that the medicine contained in their biologically inert material can be released into body tissue. By way of example, the inert material can constitute polymethyl methacrylate, and the medicine which is contained in such material can include one or more pharmaceuticals which are or which can be uniformly distributed therein. It is customary to string two or more corpuscles onto a fiament, such as a length of wire or thread, which can facilitate implantation as well as withdrawal of the thus obtained composition from an animal body.

Published German patent application No. 23 20 373 discloses spherical corpuscles. Such corpuscles can contain antibiotics and are widely used for the treatment of infections of bones and/or other parts of bodies. An advantage of such procedure is that the medicine is implanted into immediate proximity of the infected area which greatly reduces the potential undesirable effect of the implanted medicine upon other body parts, such as organs, which are not afflicted and/or should not be influenced by certain types of medicines.

European patent application No. 0 157 909 discloses corpuscles having a spheroidal shape (i.e., they constitute ellipsoids of revolution). This is intended to ensure a more satisfactory surface-to-volume relationship than in the event of the utilization of spherical corpuscles. However, the making of spheroidal corpuscles is more complicated and more expensive. Furthermore, it was ascertained that the clinical application of spheroidal corpuscles does not invariably ensure the required concentration of medicine in the afflicted tisue, namely a concentration which is required to ensure the achievement of satisfactory therapeutical results. Thus, the utilization of such corpuscles does not ensure a sufficient increase of the rate of accurately controlled release of medicine well beyond that which can be achieved by resorting to spherical corpuscles. Furthermore, controlled release of medicine is particularly difficult when the corpuscles must be implanted into certain parts of an animal body.

Attempts to make corpuscles having one or more pointed portions or sections have net with little success, primarily because the making of such corpuscles presents many problem and contributes significantly to their cost.

Another drawback of presently known corpuscles (namely those having a spherical or spheroidal shape) is that they cause the neighboring tissue to fill up or bulge so that they cannot be readily implanted immediately beneath the skin or between the skin and a bone which is closely adjacent the skin. Similar problems arise when spherical or spheroid corpuscles are to be applied to auxiliary osteosynthetic instruments or implements or parts. Furthermore, spherical and/or spheroidal corpuscles cannot be confined in large quantities in bone cavities because too much empty space necessarily remains between the abutting corpuscles of such configuration. This, in turn, exerts an adverse influence upon the quantities of medicine which can be released in the interior of a bone.

The quantities of medicine which can be released by the biologically inert material of a corpuscle depend upon the area of the external surface of the corpuscle. As a rule, the initial stage involves the release of medicine from the zones immediately adjacent the exposed surface of a corpuscle, i.e., the clinically relevant release during the first days following the implantation of a string of corpuscles is not influenced, or is not noticeably influenced, by the medicine which is confined and distributed in the central portion or core of a corpuscle. It can be said that corpuscles having spherical surfaces or surfaces having circular cross-sectional outlines in several planes which are normal to each other and bisect the corpuscles can release only relatively small percentages of medicine which is distributed in their biologically inert material.

Still another problem which is encountered when one utilizes strings of presently known spherical or spheroidal corpuscles is that they cannot be readily withdrawn from the body. The filaments which maintain a file of corpuscles close to each other are used for withdrawal of the corpuscles in response to the exertion of a pull. Such withdrawal is frequently difficult or impossible because the healing process often involves the development of granular tissue which opposes the extraction of spherical or similar corpuscles upon completion of the healing step or when the corpuscles must be removed for other reasons. One of the reasons for such difficulties is that the cross-sectional areas of spherical or spheroid particles are relatively large.

OBJECTS OF THE INVENTION

An object of the invention is to provide a corpuscle which is configurated in such a way that its biologically inert material can release a larger percentage of the medicine which is distributed therein than heretofore known corpuscles.

Another object of the invention is to provide a corpuscle which can be more readily implanted into and withdrawn from an animal body than heretofore known corpuscles.

A further object of the invention is to provide a corpuscle with a more satisfactory surface-to-volume ratio than heretofore known and utilized corpuscles.

An additional object of the invention is to provide a corpuscle which is configurated and dimensioned in such a way that it can be implanted, with one or more similar or identical corpuscles, in body areas which cannot receive heretofore known corpuscles, and which can be readily withdrawn from such body areas after it has served its purpose.

Still another object of the invention is to provide a corpuscle which can release huge quantities of medicine immediately or shortly following its implantation in or at a body tissue.

A further object of the invention is to provide a group (such as a string) or composition of interconnected corpuscles which exhibit the above outlined features and advantages.

Another object of the invention is to provide a corpuscle which can be readily implanted close to the skin without causing pronounced or excessive bulging of those portions of the skin which overlie the corpuscle.

An additional object of the invention is to provide corpuscles which can be implanted in close or immediate proximity to a bone even if the bone is closely adjacent the skin, and such positioning of the corpuscles is not likely to cause the development of pressure-induced tumors or other afflictions.

Still another object of the invention is to provide a novel and improved method of manipulating a corpuscle of the: above outlined character during implantation into and/or during withdrawal from an animal body.

A further object of the invention is to provide a novel and improved method of making and utilizing a composition of a plurality of corpuscles each of which comprises a carrier consisting at least in part of a biologically inert material and a medicine selected for localized treatment of body tissue diseases and being releasably confined and distributed in the material of the carrier.

SUMMARY OF THE INVENTION

One feature of the invention resides in the provision of a composition of a plurality of corpuscles wherein at least one corpuscle comprises a carrier of biologically inert material and a medicine for the treatment of body tissue. The medicine is releasably confined and distributed in the inert material, and the carrier has an elongated passage (e.g., a hole) for a filament (such as a wire or a thread). The configuration of the carrier departs from that of a spheroid (i.e., ellipsoid of revolution), and the external surface of the carrier includes tapering (e.g., curved) first and second portions of the first and second open ends of the passage. At least one of the first and second portions of the external surface has an arcuate outline (at least in part) in at least one transverse plane which crosses and is or can be normal to the passage.

The corpuscle can be strung onto a filament with one or more similar or identical corpuscles and can be used for localized internal or external treatment of body tissue. The medicine is or can be at least substantially uniformly distributed in the inert material of the carrier.

The carrier is or can be elongated in a direction from one toward the other open end of the passage and can include at least two different sections. One of these sections is nearer to one open end than to the other open end, and the outlines of the two sections in a longitudinal plane which bisects the carrier and is located at least close to the passage have curvatures which are or which can be different from one another.

The arrangement can be such that the carrier can include at least three sections one of which is adjacent one open end and another of which is adjacent the other open end of the passage. The outlines of the at least three sections in the aforementioned longitudinal plane can be selected in such a way that the outline of a first section of the at least three sections is different from the outline of a second section and/or a third section of the at least three sections.

The configuration of the carrier can be such that a cross-sectional outline of the carrier in the aforementioned longitudinal plane includes two portions which are at least partially arcuate and have different curvatures. Alternatively, such cross-sectional outline can include at least three different portions one of which has a first curvature and at least one other portion of the at least three portions has a second curvature different from the first curvature.

The carrier can comprise first and second sections one of which is adjacent one open end and the other of which is adjacent the other open end of the passage, and a further section disposed between the first and second sections and having the shape of a roller (e.g., a cylinder). Alternatively, the further section can resemble a barrel, or it can have an at least partially concave external surface or a substantially elliptical outline, as seen in the aforementioned longitudinal plane.

The cross-sectional outline of the carrier in the aforementioned longitudinal plane can constitute, at least in part, a second plane or second order curve.

The cross-sectional outline of at least one of the two sections which are adjacent the open ends of the passage (again in the aforementioned longitudinal plane) can constitute a second-, third-, or another higher plane curve.

At least one of the two sections which are adjacent the open ends of the passage can have a substantially conical or conoidal cross-sectional outline in the aforementioned longitudinal plane. Alternatively, at least one of these sections can have an at least substantially concave outline.

Still further, it is possible to design the corpuscle in such a way that its carrier has a first cross-sectional outline in the aforementioned longitudinal plane, and a different second cross-sectional outline in a second longitudinal plane which also bisects the carrier, which is also disposed at least close to the passage, and which is inclined relative to the first mentioned longitudinal plane.

The cross-sectional outline of the carrier in at least one of the longitudinal planes can have one or more straight portions.

The cross-sectional outline of the carrier in the aforementioned transverse plane, or in a plane which is parallel to such transverse plane, can depart from a circular or truly circular outline.

The carrier can at least resemble an ellipsoid with different dimensions as measured in the direction of two or all three main axes of such carrier.

At least a portion of the external surface of the carrier can be rough or roughened, e.g., by the provision therein of ribs and/or grooves.

The medicine which is distributed in the biologically inert material of the carrier can be an anti-inflammation or anti-tumor pharmaceutical, for example, an antibiotic, antiseptic, corticoid, antiphlogistic or cytostatic substance.

Another feature of the invention resides in the provision of a method of making and utilizing a composition of a plurality of corpuscles each of which comprises a carrier consisting at least in part of a biologically inert material and having an external surface, and a medicine selected for localized treatment of body tissue diseases and being releasably confined and distributed in the material of the carrier. The improved method comprises the steps of providing each carrier with an elongated passage having first and second open ends, imparting to the carriers a configuration other than an exact spheroid configuration including providing the external surfaces of the carriers with tapering first and second portions at the first and second open ends of the respective passages, imparting to at least one of the first and second portions of each external surface an arcuate outline in at least one transverse plane crossing the respective passage, assembling the carriers on a filament which extends through the passages of the assembled carriers, surgically implanting the assembled carriers into a diseased body tissue, leaving the assembled carriers in the diseased body tissue for a period of time sufficient to enable the medicine to treat the body tissue, and surgically removing the carriers from the treated body tissue.

The method can further comprise the step of at least substantially uniformly distributing the medicine in the material of the carrier prior to the imparting steps.

At least one of the imparting steps can include elongating each carrier in a direction from one toward the other open end of the respective passage so that each carrier comprises at least two different sections one of which is nearer to the first than to the second open end of the respective passage, that the sections have first and second outlines in at least one longitudinal plane bisecting the respective carrier and located at least close to the respective passage, and that the outlines of the sections in the at least one longitudinal plane have curvatures which are different from each other.

Furthermore, at least one of the imparting steps can include elongating each carrier in a direction from one toward the other open end of the respective passage so that each carrier comprises at least three sections one of which is adjacent the first open end and another of which is adjacent the second open end of the respective passage, that the sections have outlines located in at least one longitudinal plane bisecting the respective carrier and disposed at least close to the respective passage, and that the outline of the first section of the at least three sections in the at least one longitudinal plane is different from the outlines of the second and third sections.

Still further, at least one of the imparting steps can include providing each carrier—in at least one longitudinal plane bisecting the respective carrier and located at least close to the respective passage—with a cross-sectional outline including at least two at least partially arcuate portions having different first and second curvatures.

At least one of the imparting steps can include providing each carrier—in at least one longitudinal plane which bisects the respective carrier and is at least close to the respective passage—with a cross-sectional outline including at least three different portions comprising a first portion having a first curvature and at least one further portion having a second curvature different from the first curvature.

Still further, at least one of the imparting steps can include providing each carrier with first and second sections at the first and second open ends of the respective passage and with a substantially roller-shaped section between the first and second sections.

Moreover, at least one of the imparting steps can include providing each carrier with first and second sections at the first and second open ends of the respective passage, and with a substantially barrel-shaped section between the first and second sections.

At least one of the imparting steps can include providing each carrier with first and second sections at the first and second open ends of the respective passage, and with a third section located between the first and second sections and having an at least substantially concave external surface.

It is further within the purview of the invention to select the imparting steps in such a way that at least one thereof includes providing each carrier with first and second sections at the first and second open ends of the respective passage, and with a third section disposed between the first and second sections and having a substantially elliptical outline in a longitudinal plane bisecting the respective carrier and located at least close to the respective passage.

Furthermore, at least one of the imparting steps can include providing each carrier with a cross-sectional outline which is at least in part a second plane curve and is located in a longitudinal plane bisecting the respective carrier and disposed a least close to the respective passage.

Moreover, at least one of the imparting steps can include providing each carrier with first and second sections adjacent the first and second open ends of the respective passage, and providing at least one of the sections with a cross-sectional outline which is located in a longitudinal plane bisecting the respective carrier and at least a portion of which constitutes a higher-plane curve.

It is also possible to select the imparting steps in such a way that at least one thereof includes providing each carrier with first and second sections adjacent the first and second open ends of the respective passage, and providing at least one of the sections with a substantially conical or conoidal cross-sectional outline in a longitudinal plane bisecting the respective carrier at least close to the respective passage.

At least one of the imparting steps can include providing each carrier with first and second sections adjacent the first and second open ends of the respective passage, and providing at least one of the sections with a substantially concave outline in a longitudinal plane bisecting the respective carrier and located at least close to the respective passage.

At least one of the aforesaid imparting steps can include providing each carrier with a first cross-sectional outline located in a first longitudinal plane bisecting the respective carrier and disposed at least close to the respective passage, and with a different second cross-sectional outline located in a second longitudinal plane bisecting the respective carrier, disposed at least close to the respective passage, and being inclined relative to the first longitudinal plane.

Furthermore, at least one of the imparting steps can include providing each carrier with a cross-sectional outline which is located in a plane bisecting the respective carrier and disposed at least close to the respective passage and which has at least one substantially straight portion.

Still further, at least one of the imparting steps can include providing each carrier with a cross-sectional outline which is located in the at least one transverse plane of the respective carrier, or in a plane which is at least substantially parallel to the at least one transverse plane, and which departs from a circular cross-sectional outline.

Moreover, at least one of the imparting steps can include providing each carrier with a shape which at least resembles an ellipsoid and has three main axes and different dimensions as measured in at least two of the three main axes.

At least one of the imparting steps can include providing each carrier with a shape which at least resembles an ellipsoid and has three main axes and different dimensions in the direction of each of the three main axes.

Furthermore, at least one of the imparting steps can include roughening at least a portion of the external surface of each carrier. Such roughening step can include providing the external surface of the at least one carrier with ribs and/or grooves.

The medicine can contain an anti-inflammation pharmaceutical and/or an anti-tumor pharmaceutical and/or a pharmaceutical selected from the group consisting of antibiotics, antiseptics, corticoids, antiphlogistics and cytostatics.

The step of providing each carrier with an elongated passage can be carried out at least substantially simultaneously with at least one of the imparting and assembling steps.

The novel features which are considered as characteristic of the invention are set forth in particular in the appended claims. The improved corpuscles themselves, however, both as to their configuration and composition as well as numerous additional important and advantageous features and attributes thereof, as well as the method of making, implanting and removing the same, will be best understood upon perusal of the following detailed description of certain presently preferred specific embodiments thereof with reference to the accompanying drawings.

BRIEF DESCRIPTION OF THE DRAWINGS

FIG. 1 is a central longitudinal sectional view of a composition of three corpuscles which embody one form of the invention and are strung onto a filament of wire, thread or the like;

FIG. 2 is a greatly enlarged schematic central longitudinal sectional view of a modified corpuscle;

FIG. 3 is a similar schematic central longitudinal sectional view of a third corpuscle;

FIG. 4 is a similar central longitudinal sectional view of a fourth corpuscle;

FIG. 5 is a schematic central sectional view of a fifth corpuscle;

FIG. 6 is a cross-sectional view of a section of a corpuscle which can constitute any one of the corpuscles shown in FIGS. 1 to 5;

FIG. 7 is a similar cross-sectional view of a corpuscle with an outline having two straight and two semicircular portions;

FIG. 8 is a similar view of a section forming part of a corpuscle and having an oval cross-sectional outline; and FIG. 9 is a similar view but showing a section having a polygonal cross-sectional outline.

DESCRIPTION OF PREFERRED EMBODIMENTS

FIG. 1 shows a portion of a surgically implantable string or chain or composition of neighboring corpuscles. Though FIG. 1 actually shows only three neighboring corpuscles 1, 2 and 3, the number of such corpuscles in a composition can be less or can exceed three. The illustrated corpuscles are of identical size and shape and each thereof comprises a carrier of biologically inert material, such as polymethyl methacrylate with a suitable medicine for the treatment of body tissue incorporated therein. Such medicine is releasably confined in the material of the carrier and is or can be at least substantially uniformly distributed therein.

The corpuscles have longitudinally extending straight elongated passages 20 with open ends 20a and 20b. Such passages receive portions of an elongated flexible filament 7 which can constitute a length of thread, a length of wire or any other suitable component which can be readily introduced into the passages 20 with requisite clearances (if any are necessary) between neighboring corpuscles.

Each of the corpuscles 1, 2 and 3 is shown in a sectional view taken in a longitudinal plane which bisects the respective corpuscle and also bisects or is at least located close to the respective passage. It will be seen that the configurations of the corpuscles deviate from spherical and/or from exact spheroid configurations, and their external surfaces have end portions (one of which is adjacent the open end 20a and the other of which is adjacent the open 20b of the respective passage 20) which taper toward the filament 7 in directions toward the respective open ends. Furthermore, each of the two tapering portions of the external surface of the corpuscle 1, 2 or 3 has, at least in part, an arcuate outline in at least one transverse plane which crosses the respective passage 20. One such transverse plane is shown at 12 in FIG. 3; it extends at right angles to the respective longitudinal plane and at right angles to the longitudinal direction of the respective passage 20 at a location approximately midway between the two tapering end portions of the external surface of the corpuscle 3.

As shown in the left-hand portion of FIG. 1, each corpuscle has a substantially semispherical first section 4 adjacent the open end 20a of the passage 20, a substantially semispherical second section 6 adjacent the open end 20b, and an elongated central or median section 5 which constitutes or at least resembles a cylinder or roller and has an at least substantially polygonal (rectangular) cross-sectional outline in the longitudinal plane bisecting the respective corpuscle. The section 4 is located between the broken lines A, B which can denote planes parallel to the transverse plane 12; the section 5 is located between broken lines B, C (the line C is parallel to the lines A and B); and the section 6 is located between the broken lines C and D (the line D is parallel to the line C). If the sections 4 and 6 are true hemispheres having a common axis coinciding with the axis of the filament 7 in the passage 20, and if the central longitudinal axis of the section 5 also coincides with the axis of the filament 7 in the respective passage 20, the corresponding corpuscle 1, 2 or 3 can be said to constitute an elongated rod-shaped or cylindrical body with rounded end portions. However, it is equally within the purview of the invention to locate the passages 20 off the longitudinal central axes of the respective corpuscles; this results in the provision of corpuscles which might be more readily implanted in certain portions of a human or other animal body.

Furthermore, at least the central section 5 of each of the corpuscles 1, 2, 3 can have a cross-sectional outline as shown in FIGS. 7, 8 or 9, i.e., not necessarily just the circular outline shown in FIG. 6. Still further, it is possible to string onto the filament a series of identical and/or non-identical corpuscles, e.g., at least one series of two or more corpuscles having cross-sectional outlines as shown in FIGS. 6 and 7, 6 and 8, 6 and 9, 7 and 8, 7 and 9 or 8 and 9. The number of possible combinations is greatly increased if a filament 7 carries a string of three or more in part identical and in part different corpuscles, e.g., three corpuscles with central sections having cross-sectional outlines of the type shown in FIGS. 6, 7 and 8; 6, 7 and 9; 6, 8 and 9; and so forth. The sections shown in FIGS. 6 to 9 are taken in transverse planes such as that denoted in FIG. 1 by the line 12 extending at right angles to the longitudinal direction of the respective passage 20.

FIG. 2 shows in a schematic longitudinal sectional view a modified corpuscle 101 having a first section 104 which is different from the other two sections, a section 106 and a barrel-shaped central section 105. The external surface of the section 104 has a substantially hemispherical outline whereas the external surface of the section 106 has a Substantially semielliptical outline. The two segments 8a and 8b of the section 104 (such segments are located at the opposite sides of the passage 120) are mirror images of each other. The same applies for the segments 9a, 9b of the section 105, as well as for the segments 10a, 10b of the section 106. The length of the section 105 between the broken lines B and C may but need not exceed the length of the section 104 and/or the length of the section 106 and/or the combined length of the sections 104 and 106 (all as seen in the longitudinal direction of the passage 120).

It is equally possible to modify the corpuscle 101 in such a way that the segment 8a is not a mirror image of the segment 8b (with reference to a plane which is normal to the plane of FIG. 2 and includes the axis of the filament 7 in the passage 120), that the segment 9a is not a mirror image of the segment 9b and/or that the segment 10a is not a mirror image of the segment 10b.

The illustrated halves of the cross-sectional outline of the section 105 are or can constitute portions of an ellipse. The cross-sectional configuration of the section 105 in the plane denoted by the transverse line 12 of FIG. 2 can correspond to that shown in FIGS. 6, 7, 8 or 9.

The corpuscle 201 of FIG. 3 has a carrier of biologically inert material including a section 204 having two different segments 13a, 13b one of which has a conical or slightly convex cross-sectional outline and the other of which has a concave cross-sectional outline. In other words, the segments 13a, 13b of the section 204 are not mirror images of each other. The cross section of the median or central section 205 of the corpuscle 201 in a transverse plane denoted by the line 12 of FIG. 3 can resemble that shown in FIGS. 6, 7, 8 or 9. The segments 14a, 14b of the section 205 are not mirror images of each other. The section 206 is a cone having two segments 15a, 15b which are or which can be mirror images of each other.

The section 204 can be said to resemble the frustum of a cone, the section 206 can be said to constitute or resemble a cone, and the section 205 can be said to resemble a roller with an external surface including a concave portion and a cylindrical portion. The corpuscle 201 is an example of corpuscles wherein the segments of fewer than all sections are mirror images of each other.

The corpuscle 301 of FIG. 4 has an elliptical cross-sectional outline in the longitudinal plane which includes the axis of the filament in the passage 320. The transverse plane denoted by the line 12 divides the corpuscle 301 into two sections which are mirror images of each other in such transverse plane, and each of these sections has two segments 16a, 16b which are mirror images of each other with reference to a longitudinal plane which is normal to the plane of FIG. 4 and includes the axis of the filament 7. However, it is within the purview of the present invention to provide at least one of the two sections of the corpuscle 301 with segments which are not mirror images of each other. The cross-sectional outline of the corpuscle 301 in the transverse plane denoted by the line 12 can resemble that shown in FIGS. 6, 7, 8, or 9.

The characters a, b and c denote in FIG. 4 the three major axes of the corpuscle 301. The dimensions of the corpuscle 301 as measured in the direction of the axes b and c are the same but different from the dimension as measured in the direction of the axis a provided that the cross-sectional outline in the transverse plane denoted by the line 12 resembles that shown in FIG. 6. If one selects a cross-sectional outline as shown in FIGS. 7, 8 or 9, the dimensions as measured in the directions of all three major axes a, b and c are different.

FIG. 5 shows a corpuscle 401 having a carrier with a circular cross-sectional outline in the plane of FIG. 5, i.e., in a plane including the axis of the filament 7. The dimensions of the corpuscle in the directions of all three major axes would be identical if the cross-sectional outline of the corpuscle in any plane including the center of the corpuscle were to resemble that shown in FIG. 6. If the cross-sectional outline of FIGS. 7, 8 or 9 is chosen, the dimensions as measured in the direction of at least one of the three major axes are different from the dimensions as measured along the other major axis or axes. The corpuscle 401 of FIG. 5 is of conventional configuration only if the dimensions as measured in the direction of all three major axes are identical.

As already mentioned above, FIG. 6 shows a section through a corpuscle 30a having a circular cross-sectional outline with the center located on the axis of the filament 7. Such cross-section can be resorted to in shaping the corpuscle 1, 2 or 3 (see the line 12 in FIG. 1), the corpuscle 101 (line 12 in FIG. 2), the corpuscle 201 (line 12 in FIG. 3), the corpuscle 301 (line 12 in FIG. 4), and/or the corpuscle 401 (see the line 12 in FIG. 5).

Alternatively, and as already pointed out above, at least one of the corpuscles can have a cross sectional outline resembling or identical with that of the corpuscle 30b shown in FIG. 7. This outline has two parallel straight portions and two arcuate (e.g., semicircular) portions alternating with the straight portions as seen in the circumferential direction of the corpuscle. The major axis a of the corpuscle 30b can be greater than the major axis b and the major axis b is greater than the major axis c.

The corpuscle 30c of FIG. 8 has an elliptical cross-sectional outline. The longest major axis of the corpuscle 30c can be the axis a or the axis b, and the axis b is longer than the axis c. For the directions of the major axes reference should be had again to FIG. 4.

The cross-sectional outline of the corpuscle 30d shown in FIG. 9 is a polygon with slightly rounded corners.

The illustrated corpuscle 30d has a substantially rectangular cross-sectional outline with two pairs of straight parallel sides. The major axis b and/or a is or can be longer than the major axis c. For example, the axis a can be longer than the axis b.

An important advantage of the improved corpuscles (for example, of corpuscles 1, 2, 3 with cross-sectional outlines corresponding to that shown in FIG. 7 or FIG. 9) is that the surface-to-volume ratio of their carriers is much more satisfactory than if one employs spherical or exactly spheroidal corpuscles. As a rule, the medicine which is distributed at the center of an improved corpuscle (e.g., a corpuscle whose carrier has a circular outline in a longitudinal or transverse plane) constitutes a small percentage of the overall quantity of medicine so that, from the clinical standpoint, the influence of such small percentage of medicine upon the healing process can be disregarded. This can be taken into consideration in connection with the distribution of medicine in the biologically innert material of the carriers to thus achieve at least some savings in medicine.

The fact that the improved corpuscles can contain larger concentrations or larger quantities of medicine close to the surfaces of their carriers is particularly important in connection with the treatment of certain types of afflictions, for example, for the treatment of infected tissue. Certain bacteria which are the cause of such infections have developed a pronounced resistance to the action of medicine unless the medicine can be released in large quantities, and this can be accomplished by resorting to the corpuscles which embody the present invention. The ability of the novel corpuscles to release large quantities of medication to accurately selected body tissue is even more important due to the fact that the development of certain medications, such as antibiotics, did not progress much during the last years so that many bacteria have developed pronounced resistance to existing medicine, and the only presently known procedure to counteract such increased resistance is to administer larger quantities of available medicine. In fact, it is often necessary to administer enormously increased quantities of medicine. Furthermore, the ability of the improved corpuscles to contain large concentrations of medicine close to the exposed surfaces of their carriers renders it possible to implant the corpuscles in body regions which were not accessible to such therapy, or the utilization of which was not considered beneficial, by resorting to conventional corpuscles.

The improved corpuscles can be utilized with equal or similar advantage in conjunction with numerous auxiliary equipment for use in osteosynthesis, such as endoprostheses, rods, plates and others. One of the reasons is that it is not necessary to weaken such auxiliary equipment for the purpose of utilizing it with the improved corpuscles. In addition, it is possible to apply the improved corpuscles to plates or other parts which are to be implanted immediately beneath the skin without causing any problems as far as the availability of sufficient space is concerned.

Still another advantage of the improved corpuscles is that they render it possible to reduce the percentage of unoccupied space between them, i.e., it is possible to implant larger quantities of biologically inert material per unit of volume. This leaves less room for the development of granular tissue between neighboring corpuscles which, in turn, reduces the resistance which is offered by surrounding tissue to withdrawal of the implanted corpuscles. As a rule, the resistance which the tissue offers to withdrawal of a chain or string of corpuscles depends on the thickness of the tissue.

It is clear that the improved corpuscles are susceptible of numerous additional modifications without departing from the spirit of the invention. For example, the features of the corpuscles, 1, 101, 201, 301, 401 can be interchanged and/or combined and/or further modified. This holds true for the outer sections (such as 4 and 6) as well as for the central sections (such as 5) of the novel corpuscles. The overall dimensions of the improved corpuscles can approximate those of the heretofore known corpuscles.

As a rule, the passage (such as 20) in the improved corpuscle will develop as a result of shaping of the carrier of the corpuscle directly onto a filament, i.e., the passage need not be formed in advance if the carrier is shaped as a result of polymerization (or by resorting to any other suitable procedure) directly onto the filament. This simplifies the making of strings of neighboring corpuscles and simplifies the removal of such strings from the loci of implantation.

The diameter of a conventional spherical corpuscle is normally in the range of 7 mm. By way of example only, and referring to a corpuscle of the type shown at 1, 2 or 3 in FIG. 1 and assuming that the cross-sectional outline of such a corpuscle in the plane 12 resembles that shown in FIG. 7 or 9, the length of such a corpuscle (as measured along the major axis a) can be in the range of between 3 and 15 mm, the height (as measured in the direction of the axis b) can be between 1.5 and 10 mm, and the width (as measured in the direction of the axis c) can be between 1 and 5 mm.

It is presently preferred to impart to the corpuscles a shape corresponding to that of the corpuscles 1, 2, 3 shown in FIG. 1 with a cross-sectional outline as that shown in FIGS. 7, 8 or 9. Such corpuscles can be produced at a reasonable cost and their surface-to-volume ratio is highly satisfactory. The configurations shown in FIGS. 2 and 3 will be resorted to when the surface-to-volume ratio should be further increased, i.e., when the additional cost for the making of such relatively complex corpuscles is warranted in order to ensure an even more satisfactory diffusion of huge quantities of a given medicine into the adjacent tissue.

Spherical particles having a diameter of 1–20 mm are disclosed in U.S. Pat. No. 3,882,858 granted May 13, 1975 to Klaus Klemm for "SURGICAL SYNTHETIC-RESIN MATERIAL AND METHOD OF TREATING OSTEOMYELITIS". The disclosure of this patent is incorporated herein by reference.

As used herein, the term "taper" or "tapering" is not intended to denote only "to become gradually smaller" but is intended to also embrace stepwise as well as partly gradual and partly abrupt reductions of cross-sectional areas. For example, the sections 4 and 6 of the corpuscle 1 shown in FIG. 1 can have conical, convex and/or concave outlines, as seen in the longitudinal sectional plane of FIG. 1. Furthermore, and as already mentioned above, the central section 5 of any or all of the corpuscles 1, 2, 3 shown in FIG. 1 can have an outline as shown in FIGS. 6, 7, 8, or 9.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of corpluscles for the confinement of medicine and, therefore, such adaptations should and are intended to be comprehended within the meaning and range of equivalence of the appended claims.

What is claimed is:

1. A surgically implantable and removable composition of a plurality of corpuscles strung together by a filament, each of said corpuscles comprising a carrier of biologically inert material and a medicine for localized treatment of body tissue diseases, said medicine being releasably confined in and being distributed in said inert material and said carriers having elongated passages for the filament and each said passage having first and second open ends, said carriers further having configurations other than an exact spheroid configuration to facilitate removal of the implanted composition and external surfaces including tapering first and second portions at said first and second open ends, respectively, to further facilitate removal of the implanted composition, at least one of said first and second portions having, at least in part, an arcuate outline in at least one transverse plane crossing the respective passage.

2. The composition of claim 1 for localized internal or external treatment of body tissue, wherein said medicine is at least substantially uniformly distributed in said inert material.

3. The composition of claim 1, wherein each of said carriers is elongated in a direction from one toward the other of said open ends thereof and includes at least two different sections one of which is nearer to said first open end than to said second open end, said sections having first and second outlines in at least one longitudinal plane bisecting the respective carrier and located at least close to the respective passage, the outlines of said sections in said at least one longitudinal plane having curvatures which are different from one another.

4. The composition of claim 1, wherein each of said carriers is elongated in a direction from one toward the other of said open ends thereof and includes at least three sections one of which is adjacent said first open end and another of which is adjacent said second open end, said sections having outlines located in at least one longitudinal plane bisecting the respective carrier and disposed at least close to the respective passage, the outline of said first section of said at least three sections in said at least one longitudinal plane being different from the outlines of second and third sections of said at least three sections in said at least one longitudinal plane.

5. The composition of claim 1, wherein a cross-sectional outline of each of said carriers in at least one longitudinal plane bisecting the respective carrier and located at least close to the respective passage includes at least two at least partially arcuate portions having different first and second curvatures.

6. The composition of claim 1, wherein a cross-sectional outline of each of said carriers in at least one longitudinal plane which bisects the carrier and is at least close to the respective passage includes at least three different portions comprising a first portion having a first curvature, at least one of a second and a third portion of said at least three different portions having a second curvature different from said first curvature.

7. The composition of claim 1, wherein each of said carriers includes first and second sections at said first and second open ends, respectively, and a substantially roller-shaped section between said first and second sections.

8. The composition of claim 1, wherein each of said carriers includes first and second sections at said first and second open ends, respectively, and a substantially barrel-shaped section between said first and second sections.

9. The composition of claim 1, wherein each of said carriers includes first and second sections at said first and second open ends, respectively, and a section disposed between said first and second sections and having an at least partially concave external surface.

10. The composition of claim 1, wherein each of said carriers includes first and second sections at said first and second open ends, respectively, and a section disposed between said first and second sections and having a substantially elliptical outline in a longitudinal plane bisecting the carrier and located at least close to the respective passage.

11. The composition of claim 1, wherein each of said carriers has a cross-sectional outline which is at least in part a second plane curve and is located in a longitudinal plane bisecting the carrier and disposed at least close to the respective passage.

12. The composition of claim 1, wherein each of said carriers comprises first and second sections respectively adjacent said first and second open ends, at least one of said sections having a cross-sectional outline in a longitudinal plane bisecting the carrier at least close to the respective passage, at least a portion of said cross-sectional outline constituting a higher-plane curve.

13. The composition of claim 1, wherein each of said carriers includes first and second sections respectively adjacent said first and second open ends, at least one of said sections having an at least substantially conical or conoidal cross-sectional outline in a longitudinal plane bisecting the carrier at least close to the respective passage.

14. The composition of claim 1, wherein each of said carriers includes first and second sections respectively adjacent said first and second open ends, at least one of said sections having an at least substantially concave outline in a longitudinal plane bisecting the carrier and located at least close to the respective passage.

15. The composition of claim 1, wherein each of said carriers bas a first cross-sectional outline in a first longitudinal plane bisecting the carrier and disposed at least close to the respective passage, and a different second cross-sectional outline in a second longitudinal plane bisecting the carrier, disposed at least close to the respective passage and being inclined relative to said first longitudinal plane.

16. The composition of claim 1, wherein each of said carriers has a cross-sectional outline in a longitudinal plane bisecting the carrier and disposed at least close to the respective passage, said cross-sectional outline having at least one substantially straight portion.

17. The composition of claim 1, wherein each of said carriers has a cross-sectional outline located in said a least one transverse plane, or a plane at least substantially parallel to said at least one transverse plane, and departing from a circular cross-sectional outline.

18. The composition of claim 1, wherein each of said carriers at least resembles an ellipsoid having three main axes and having different dimensions as measured in the direction of at least two of said axes.

19. The composition of claim 1, wherein each of said carriers at least resembles an ellipsoid having three main axes and having different dimensions in the direction of each of said axes.

20. The composition of claim 1, wherein at least a portion of each of said external surfaces is rough.

21. The composition of claim 20, wherein said rough portion of each of said external surfaces is ribbed.

22. The composition of claim 20, wherein said rough portion of each of said external surfaces is grooved.

23. The composition of claim 1, wherein the medicine contains an anti-inflammation pharmaceutical.

24. The composition of claim 1, wherein the medicine contains an anti-tumor pharmaceutical.

25. The composition of claim 1, wherein the medicine contains a pharmaceutical selected from the group consisting of antibiotics, antiseptics, corticoids, antiphlogistics and cytostatics.

26. A method of making and utilizing a composition of a plurality of corpuscles each of which comprises a carrier consisting at least in part of a biologically inert material and having an external surface, and a medicine selected for localized treatment of body tissue diseases and being releasably confined and distributed in the material of the carrier, comprising the steps of:

providing each carrier with an elongated passage having first and second open ends;

imparting to the carriers a configuration other than an exact spheroid configuration, including providing the external surfaces of the carriers with tapering first and second portions at the first and second open ends of the respective passages;

imparting to at least one of the first and second portions of each external surface an arcuate outline in at least one transverse plane crossing the respective passage;

assembling the carriers on a filament which extends through the passages of the assembled carriers;

surgically implanting the assembled carriers into a diseased body tissue;

leaving the assembled carriers in the diseased body tissue for a period of time sufficient to enable the medicine to treat the body tissue; and surgically removing the carriers from the treated body tissue.

27. The method of claim 26, further comprising the step of at least substantially uniformly distributing the medicine in the material of the carriers prior to said imparting steps.

28. The method of claim 26, wherein at least one of said imparting steps includes elongating each carrier in a direction from one toward the other open end of the respective passage so that each carrier comprises at least two different sections one of which is nearer to the first than to the second end of the respective passage, that the sections have first and second outlines in at least one longitudinal plane bisecting the respective carrier and located at least close to the respective passage, and that the outlines of the sections in the at least one longitudinal plane have curvatures which are different from each other.

29. The method of claim 26, wherein at least one of said imparting steps includes elongating each carrier in a direction from one toward the other open end of the respective passage so that each carrier comprises at least three sections one of which is adjacent the first open end and another of which is adjacent the second open end of the respective passage, that the sections have outlines located in at least one longitudinal plane bisecting the respective carrier and disposed at least close to the respective passage, and that the outline of the first section of the at least three sections in the at least one longitudinal plane is different from the outlines of the second and third sections.

30. The method of claim 26, wherein at least one of said imparting steps includes providing each carrier—in at least one longitudinal plane bisecting the respective carrier and located at least close to the respective passage—with a cross-sectional outline including at least two at least partially arcuate portions having different first and second curvatures.

31. The method of claim 26, wherein at least one of said imparting steps includes providing each carrier—in at least one longitudinal plane which bisects the respective carrier and is at least close to the respective passage—with a cross-sectional outline including at least three different portions comprising a first portion having a first curvature and at least one further portion having a second curvature different from the first curvature.

32. The method of claim 26, wherein at least one of said imparting steps includes providing each carrier with first and second sections at the first and second open ends of the respective passage, and with a substantially roller-shaped section between the first and second sections.

33. The method of claim 26, wherein at least one of said imparting steps includes providing each carrier with first and second sections at the first and second open ends of the respective passage, and with a substantially barrel-shaped section between the first and second sections.

34. The method of claim 26, wherein at least one of said imparting steps includes providing each carrier with first and second sections at the first and second open ends of the respective passage, and with a third section located between the first and second sections and having an at least substantially concave external surface.

35. The method of claim 26, wherein at least one of said imparting steps includes providing each carrier with first and second sections at the first and second open ends of the respective passage, and with a third section disposed between the first and second sections and having a substantially elliptical outline in a longitudinal plane bisecting the respective carrier and located at least close to the respective passage.

36. The method of claim 26, wherein at least one of said imparting steps includes providing each carrier with a cross-sectional outline which is at least in part a second plane curve and is located in a longitudinal plane bisecting the respective carrier and disposed at least close to the respective passage.

37. The method of claim 26, wherein at least one of said imparting steps includes providing each carrier with first and second sections adjacent the first and second open ends of the respective passage, and providing at least one of the sections with a cross-sectional outline which is located in a longitudinal plane bisecting the respective carrier and at least a portion of which constitutes a higher-plane curve.

38. The method of claim 26, wherein at least one of said imparting steps includes providing each carrier with first and second sections adjacent the first and second open ends of the respective passage, and providing at least one of the sections with a substantially conical or conoidal cross-sectional outline in a longitudinal plane bisecting the respective carrier at least close to the respective passage.

39. The method of claim 26, wherein at least one of said imparting steps includes providing each carrier with first and second sections adjacent the first and second open ends of the respective passage, and providing at least one of the sections with a substantially concave outline in a longitudinal plane bisecting the respective carrier and located at least close to the respective passage.

40. The method of claim 26, wherein at least one of said imparting steps includes providing each carrier with a first cross-sectional outline located in a first longitudinal plane bisecting the respective carrier and disposed at least close to the respective passage, and with a different second cross-sectional outline located in a second longitudinal plane bisecting the respective carrier, disposed at least close to the respective passage, and being inclined relative to the first longitudinal plane.

41. The method of claim 26, wherein at least one of said imparting steps includes providing each carrier with a cross-sectional outline which is located in a plane bisecting the respective carrier and disposed at least close to the respective passage and which has at least one substantially straight portion.

42. The method of claim 26, wherein at least one of said imparting steps includes providing each carrier with a cross-sectional outline which is located in the at least one transverse plane of the respective carrier, or in a plane at least substantially parallel to the at least one transverse plane, and which departs from a circular cross-sectional outline.

43. The method of claim 26, wherein at least one of said imparting steps includes providing each carrier with a shape which resembles an ellipsoid and has three main axes and different dimensions as measured in at least two of the three main axes.

44. The method of claim 26, wherein at least one of said imparting steps includes providing each carrier with a shape which at least resembles an ellipsoid and has three main axes and different dimensions in the direction of each of the three main axes.

45. The method of claim 26, wherein at least one of said imparting steps includes roughening at least a portion of the external surface of each carrier.

46. The method of claim 45, wherein said roughening step includes providing the external surface of at least one carrier with ribs.

47. The method of claim 45, wherein said roughening step includes providing the external surface of at least one carrier with grooves.

48. The method of claim 26, wherein the medicine contains an anti-inflammation pharmaceutical.

49. The method of claim 26, wherein the medicine contains an anti-tumor pharmaceutical.

50. The method of claim 26, wherein the medicine contains a pharmaceutical selected from the group consisting of antibiotics, antiseptics, corticoids, antiphlogistics and cytostatics.

51. The method of claim 26, wherein said step of providing each carrier with an elongated passage is carried out at least substantially simultaneously with at least one of said imparting and assembling steps.

* * * * *